United States Patent
Deverre

(10) Patent No.: US 7,131,958 B2
(45) Date of Patent: Nov. 7, 2006

(54) PLACENTAL BLOOD COLLECTION LINE INCLUDING A RINSING BAG

(75) Inventor: Frederic Deverre, Lille (FR)

(73) Assignee: MacoPharma, Mouvaux (FR)

( * ) Notice: Subject to any disclaimer, the term of this patent is extended or adjusted under 35 U.S.C. 154(b) by 494 days.

(21) Appl. No.: 10/160,756

(22) Filed: May 31, 2002

(65) Prior Publication Data

US 2002/0183679 A1    Dec. 5, 2002

(30) Foreign Application Priority Data

Jun. 1, 2001    (FR) .................................. 01 07262

(51) Int. Cl.
| A61M 37/00 | (2006.01) |
| A61M 1/36 | (2006.01) |
| A31B 19/00 | (2006.01) |

(52) U.S. Cl. ...................... 604/6.15; 422/44; 604/408; 604/410

(58) Field of Classification Search ................ 604/403, 604/408, 410, 411, 416, 317, 6.05, 6.03, 262, 604/6.16, 326, 327, 6.15, 19; 210/252, 781, 210/782, 257.1; 383/210.1; 206/363–366; 435/2

See application file for complete search history.

(56) References Cited

U.S. PATENT DOCUMENTS

| 4,850,995 A | 7/1989 | Tie et al. ....................... 604/6 |
| 5,789,147 A * | 8/1998 | Rubinstein et al. ............. 435/2 |
| 5,879,318 A * | 3/1999 | Van Der Heiden et al. ...... 604/6.02 |
| 6,059,968 A * | 5/2000 | Wolf, Jr. ...................... 210/252 |
| 6,488,860 B1 * | 12/2002 | Mari et al. ................... 210/806 |
| 2004/0048372 A1 * | 3/2004 | Hariri ........................ 435/366 |

OTHER PUBLICATIONS

European Patent Application No. EP0987034A2; Yoshitaka Ohmura, "Apparatus and Method for Isolating and Recovering Cells", Sep. 13, 1999.

* cited by examiner

*Primary Examiner*—Tatyana Zalukaeva
*Assistant Examiner*—Leslie R. Deak
(74) *Attorney, Agent, or Firm*—Baker Botts L.L.P.; Paul R. Morico

(57) ABSTRACT

The invention relates to a placental blood collection line including a collection bag (1) in fluid communication with at least one collection needle (4, 5) via a first tube (2) associated with an inlet orifice (3) of the bag (1), said line further including a bag (6) containing a rinsing solution and which is connected to or is organized to be connected to said first tube (2) via a second tube (7). The invention also relates to a method of collecting placental 10 blood by using such a line.

24 Claims, 2 Drawing Sheets

PLACENTAL BLOOD COLLECTION LINE INCLUDING A RINSING BAG

CROSS REFERENCE TO RELATED APPLICATION

This application claims priority to French application number 0107262 filed Jun. 1, 2001.

The invention relates to a blood collection line for collecting placental blood, and to a method of collecting placental blood using said line.

It is typically applicable to collecting hematopoietic stem cells (HSCs) present in placental blood. HSCs are at the core of new cellular therapies, in particular in the form of transplants to patients suffering from congenital or acquired hematological diseases such as cancer or leukemia. Recent scientific trials have shown that transplanting HSCs from placental blood constitutes therapeutic treatment that is of very high quality, in particular because of the very high proliferation of the injected cells and because the number of rejections is much lower than the numbers of rejections obtained with the other sources of such cells.

For collecting placental blood, systems are known, in particular from Document U.S. Pat. No. 5,879,318, in which a collection bag is associated with one or two collection needles.

That type of system suffers, in particular, from the drawback that it enables only a small quantity (about 100 milliliters (ml)) of placental blood, and therefore only a small quantity of HSCs, to be collected, which does not make it possible to transplant to adults.

In addition, when the blood is not collected optimally, the volume collected is insufficient for it to be used in cellular therapy.

An object of the invention is thus to remedy those drawbacks by proposing, in particular, a blood collection line for collecting placental blood that makes it simple under closed circuit and sterile conditions, to collect a larger quantity of blood in order to offer clinicians therapeutic doses of HSCs that are higher, thereby opening up the possibility of using HSCs from umbilical cord blood for transplants to adults.

To this end, and in a first aspect, the invention provides a placental blood collection line including a collection bag in fluid communication with at least one collection needle via a first tube associated with an inlet orifice of the bag, said line further including a bag containing a rinsing solution and which is connected to or is organized to be connected to said first tube via a second tube.

In a second aspect, the invention provides a method of collecting placental blood by using such a blood collection line, said method comprising the following steps:

- optionally connecting the bag containing the rinsing solution;
- forming a first tap into a vein of the umbilical cord or into the placenta with a needle;
- collecting the placental blood in the collection bag;
- emptying the bag containing the rinsing solution into the umbilical cord and into the placenta via the inserted needle;
- forming a second tap into the vein of the umbilical cord or into the placenta with the same needle or with another needle;
- collecting placental blood optionally together with added rinsing solution in the collection bag;
- optionally inserting anticoagulant and/or preservative solution into the collection bag.

Other objects and advantages of the invention will appear on reading the following description given with reference to the accompanying drawings, in which.

FIGS. 1 to 4 show a blood collection line including a collection bag 1 in fluid communication with at least one collection needle 4, 5 via a first tube 2 associated with an inlet orifice 3 of the bag 1.

This line typically serves to collect placental blood. For this purpose, the needle 4, 5 is inserted into a vein of the umbilical cord C in order to cause placental blood to flow under gravity into the collection bag 1.

In a first practice, the placental blood is collected during childbirth so that the mother's contractions help the blood to flow into the collection bag 1.

In a second practice, after the placenta P has been expelled, and after the umbilical cord C has been separated from the child, the placenta P is placed on a worktop T from which the umbilical cord C is left to hang down in order to enable the blood to be collected under gravity.

Figure 2:
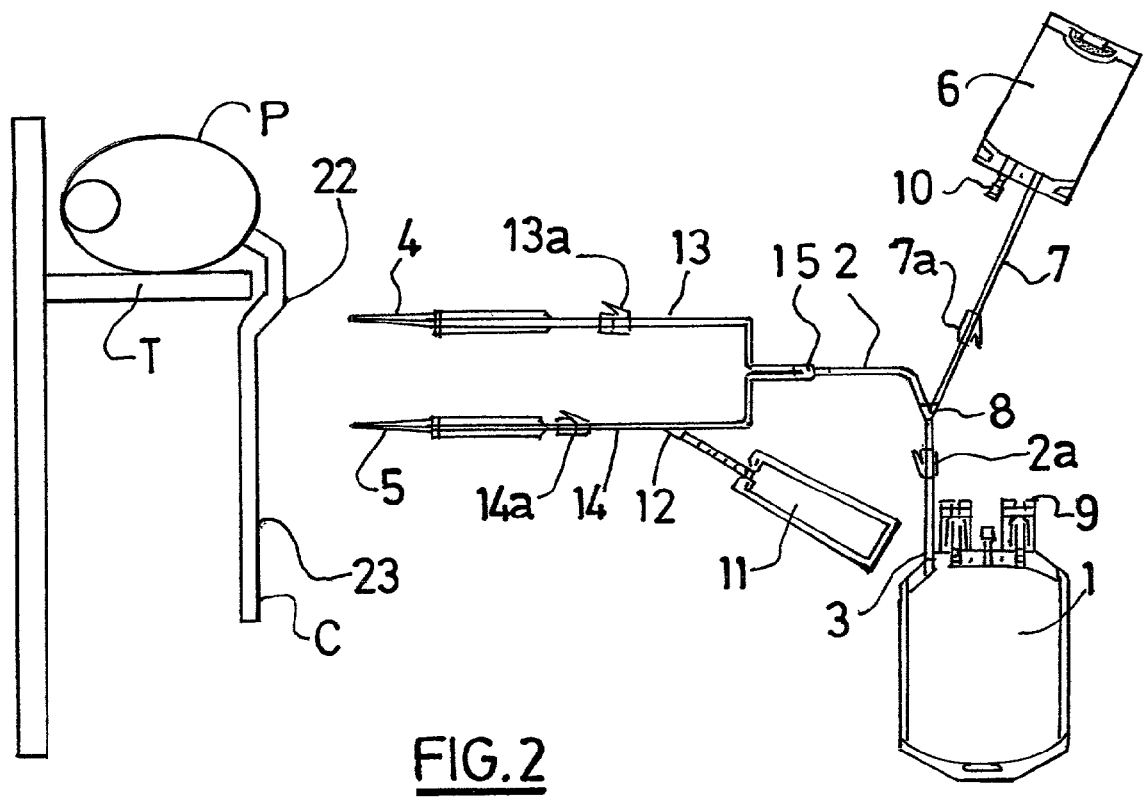
FIG. 2 is a diagrammatic front view of a second embodiment of a blood collection line of the invention.

Although FIG. 2 shows the second practice only, the blood collection line of the invention can also be used for the first practice.

The line further includes a "rinsing" bag 6 containing a rinsing solution, e.g. formed of an aqueous solution of sodium chloride or of any other solution that is inert for blood. As explained below, this bag 6 makes it possible to collect a larger quantity of placental blood than is possible with prior art blood collection lines.

Typically, the rinsing bag 6 contains a quantity of rinsing solution lying in the range 30 ml to 2 liters (l) so as to enable the umbilical cord C and the placenta P to be rinsed.

In a first variant (shown in the figures), the rinsing bag 6 is provided with a second tube 7 which is connected to the first tube 2 via a first coupling 8, e.g. a T or Y coupling.

In a second variant (not shown), the rinsing bag 6 serves to be associated with the line, e.g. immediately before collection. To this end, the second tube 7 is provided with connection means, e.g. sterile connection means or connection means in the form of a Luer connector or of a perforator, for connecting it to the first tube 2.

In both of these variants, collection is performed under closed circuit and sterile conditions in order to avoid any bacterial contamination of the collected blood.

The bags are typically made up of two sheets of plastic assembled together, e.g. by sealing, over their outside periphery so as to define an internal volume and inlet and/or outlet orifices.

The sheets are made of a plastics material that is flexible, biocompatible, sealable, and sterilizable, e.g. polyvinyl chloride.

Each of the inlet and/or outlet orifices is organized to receive a tube in leaktight manner, or is closed off in leaktight and sterile manner by a device 9 which can be torn off when the operator wishes to use the orifices.

The rinsing bag 6 may also be provided with an injection port 10 in order to enable a substance to be injected into the rinsing solution.

In the embodiments shown, the line further includes a bag 11 containing an anticoagulant and/or preservative solution for the collected blood, e.g. of the citrate-phosphate-dextrose (CPD) type.

Figure 1:
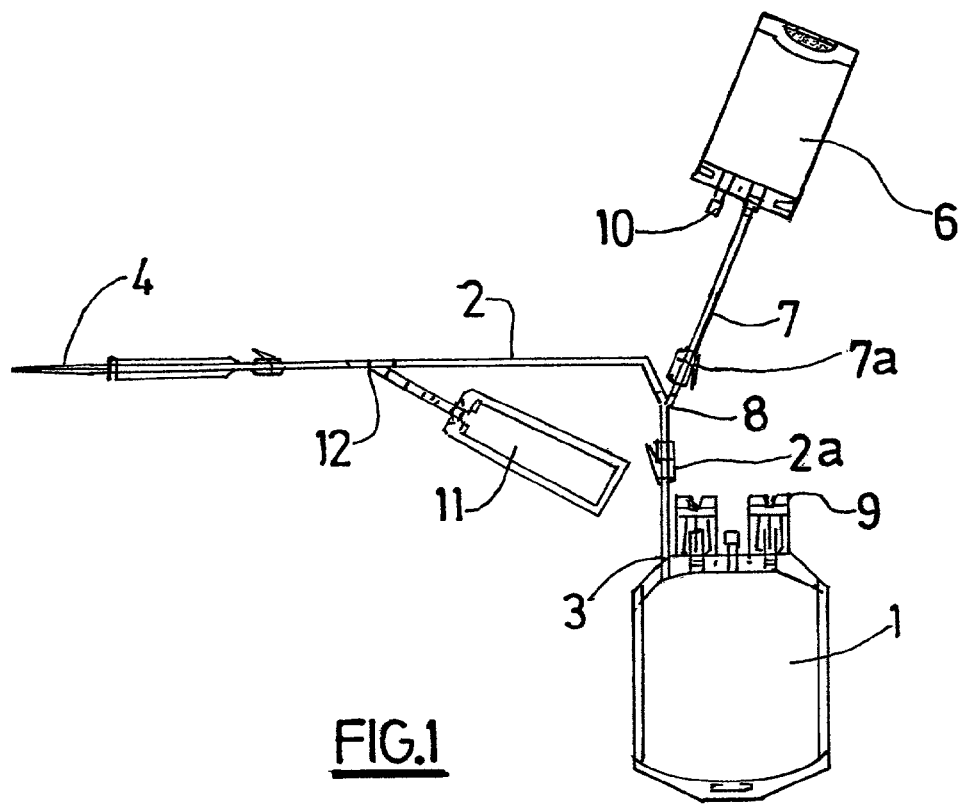
FIG. 1 is a diagrammatic front view of a first embodiment of a blood collection line of the invention.

In the first embodiment shown in FIG. 1, the bag 11 is connected to the first tube 2 via a third coupling 12 provided in the vicinity of the needle 4.

Although this embodiment makes it possible, at the end of collection, to rinse out the first tube 2 with the anticoagulant and/or preservative solution, and thus to increase the quantity of blood collected, it is possible to make provision for the collection bag 1 to contain the anticoagulant and/or preservative solution as of being manufactured.

Figure 3:
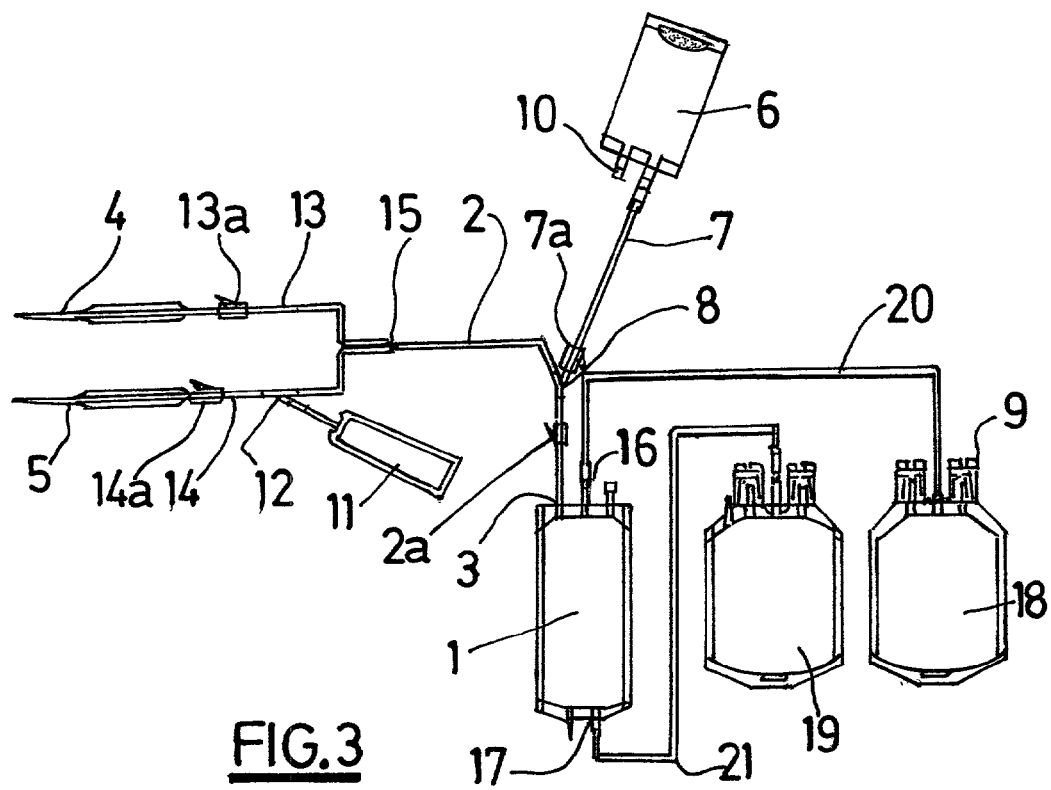
FIG. 3 is a diagrammatic front view of a third embodiment of a blood collection line of the invention.
Figure 4:
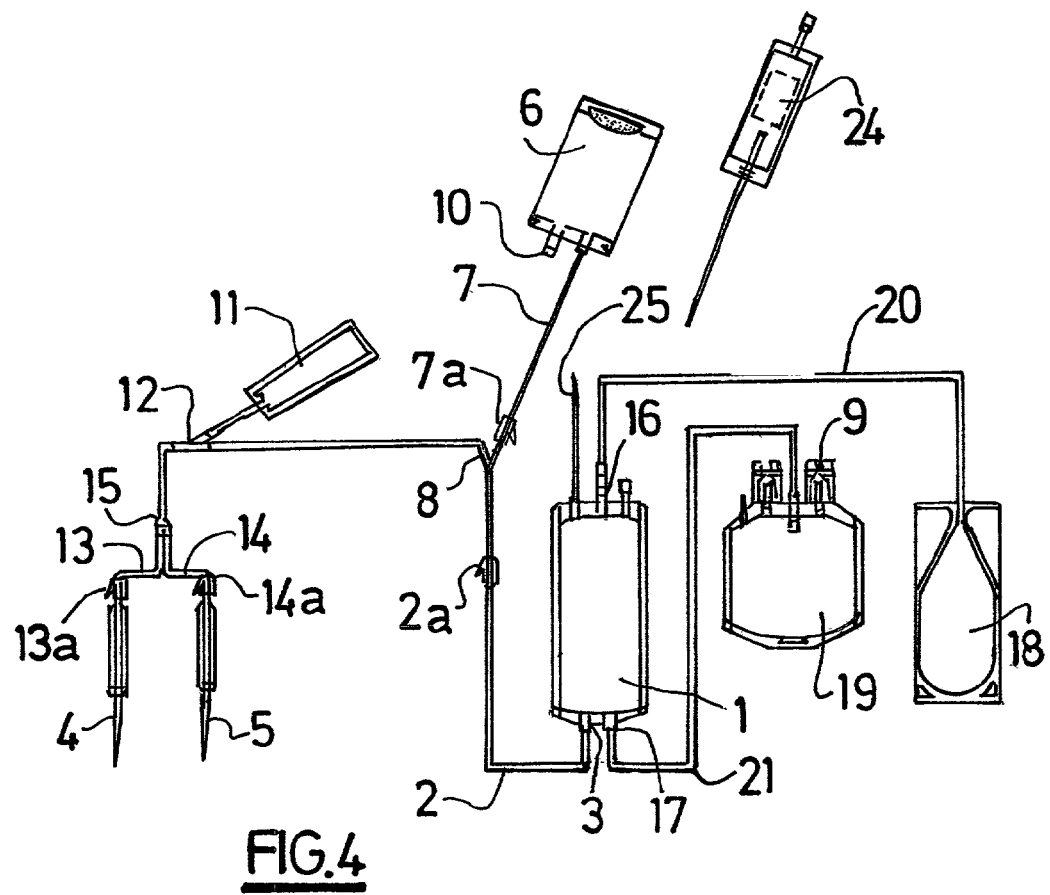
FIG. 4 is a diagrammatic front view of a fourth embodiment of a blood collection line of the invention.

A description follows of the three embodiments shown respectively in FIGS. 2 to 4, in which the line includes first and second collection needles 4 and 5.

As explained in the description below, this embodiment makes it easier to manipulate the line during collection.

The two needles 4 and 5 are in fluid communication respectively with a third tube 13 and with a fourth tube 14, said third and fourth tubes 13 and 14 being associated with the first tube 2 via a second coupling 15.

In the second and third embodiments (FIGS. 2 and 3), the bag 11 containing the anticoagulant and/or preservative solution is associated with the fourth tube 14, while in the fourth embodiment (FIG. 4), it is associated with the first tube 2 in the vicinity of the second coupling 15. These two embodiments make it possible to wash the tubes that have been used to collect the placental blood with the anticoagulant and/or preservative solution.

In the third and fourth embodiments, the collection bag 1 is provided with two outlet orifices 16, 17 provided respectively in the top and in the bottom of the bag 1, a first bag 18 and a second bag 19 being provided to be in fluid communication with respective ones of these orifices 16, 17 via respective tubes 20, 21.

The tubes are flexible, breakable, and sealable, and each of them is provided with selective opening/closure means, e.g. in the form of a clamp 2a, 7a, 13a, and 14a for selectively opening up/closing off the fluid communication through the tube.

A method of collecting placental blood by using a line of the invention is described below.

In a first step, and when it is not connected to the line as of being manufactured, the bag containing the rinsing solution 6 is connected to the line in sterile manner.

Then, for example after disposing the placenta P on a worktop (see FIG. 2) and ligaturing the free end of the umbilical cord C, a first tap into an umbilical vein or into the placenta P is performed. For example, a needle 4 is inserted into a top portion 22 of a vein of the umbilical cord. The term "top" is used to mean in the vicinity of the placenta P.

In the embodiments in which two needles 4, 5 are provided, it is the top first needle 4 that is inserted first (see FIG. 2).

On opening the clamps 13a and 2a, placental blood then flows under gravity into the collection bag 1.

Once this flow is finished, the clamp 2a is closed and the clamp 7a is opened in order to empty the bag 6 containing the rinsing solution via the inserted needle 4 into the umbilical cord C and into the placenta P.

By injecting the rinsing solution in this way, it is possible to rinse out the umbilical vein and thus to recover a larger quantity of placental blood. In addition, it makes it possible to increase the pressure inside the placenta P, thereby obtaining a corresponding increase in the expulsion of the blood contained therein.

In a subsequent step, a second tap into the umbilical vein or into the placenta P is performed. For example, a bottom portion 23 (i.e. a portion distant from the placenta) of the vein of the umbilical cord C is pricked.

In the first embodiment, the needle 4 is firstly withdrawn from the top portion 22 so as to be inserted into the bottom portion 23, while in the other three embodiments, it is the second needle 5 that is inserted into the bottom portion 23.

The use of two needles 4, 5 makes it easier to manipulate the transfusion line by organizing the length(s) of the third and fourth tubes 13 and 14 to enable the first and second needles 4 and 5 to be inserted into respective ones of the top and bottom portions 22 and 23 of the umbilical vein.

In other embodiments, the first and second taps may be performed at substantially the same place or at different relative positions. In particular, and in the first embodiment, the needle 4 may be left inserted at the same place for both of the first and second taps.

By opening the clamps 14a, 2a, and by closing the clamp 7a, it is then possible to collect placental blood, optionally together with added rinsing solution, in the collection bag 1.

The fact that provision is made to prick a top portion 22 of the vein to inject the rinsing solution makes it possible in particular to improve the recovery of the blood contained in the placenta P, while provision is made to collect the blood together with the added rinsing solution in a bottom portion 23 in order to increase the quantity of blood collected, in particular by increasing the flow pressure.

Trials have shown that it is possible to recover up to twice as much umbilical blood as in methods not using a rinsing solution.

When it is not present in the collection bag 1 as of manufacture, the anticoagulant and/or preservative solution is then inserted into the collection bag, by closing the clamp 14a, in order to make it possible to wash the tube 2, 14 that was used for collecting the placental blood.

In a subsequent step, the collection bag 1 may be removed from the blood collection line, e.g. by cutting and sealing off the first tube 2 in the vicinity of the inlet orifice 3.

The bag 1 containing the placental blood can then be processed, e.g. by centrifuging, so as to make it possible to reduce the volume containing the HSCs.

Under the effect of suitable centrifuging, the placental blood separates into three layers comprising respectively the plasma and optionally the rinsing solution, the leukocytes and the HSCs (which have substantially the same density), and the red corpuscles.

To this end, in the third and fourth embodiments, first and second bags 18, 19 are associated with respective ones of top and bottom outlet orifices 16, 17 of the collection bag 1 so as to make it possible, by pressing the collection bag 1 to recover respectively the plasma layer and the concentrate of red corpuscles inside said bags.

Thus, after this step and optionally after removing the first and second bags 18, 19, e.g. by cutting and sealing the tubes 20, 21, the collection bag 1 then contains only the intermediate layer containing the leukocytes and the HSCs.

In the fourth embodiment (FIG. 4), a third bag 24 is provided to be connected in sterile manner to an outlet orifice 25 of the collection bag 1 in order to recover the contents of said collection bag.

In all of the embodiments, the collected blood or the intermediate layer may, after a cryopreservation solution such as dimethyl sulfoxide (DMSO) and a protein solution (albumin, hydroxy-ethyl-starch (HES)) have been added, be stored by being frozen, or be processed in conventional manner in order to recover the HSCs.

The invention claimed is:

1. A method of collecting placental blood comprising:
using a placental blood collection line comprising a collection bag in fluid communication with at least one collection needle via a first tube associated with an inlet orifice of the bag, said line further comprising a bag containing a rinsing solution and which is connected to said first tube via a second tube;
forming a first tap into a vein of the umbilical cord or into the placenta with a needle;
collecting the placental blood in the collection bag;
emptying the bag containing the rinsing solution into the umbilical cord and into the placenta via the inserted needle of the first tap;
rinsing the placenta from which blood has been collected with the rinsing solution;
forming a second tap into the vein of the umbilical cord or into the placenta via the same needle or with another needle;
opening the first and second taps at the same time; and
collecting placental blood together with added rinsing solution in the collection bag using the second tap.

2. A method according to claim 1, wherein the first and second tubes are interconnected via a first coupling.

3. A method according to claim 2, wherein first and second collection needles are provided in fluid communication with respective ones of third and fourth tubes, said third and fourth tubes being associated with the first tube via a second coupling.

4. A method according to claim 3, wherein each of the tubes is provided with a valve clamp.

5. A method according to claim 2, wherein each of the tubes is provided with a valve clamp.

6. A method according to claim 2, wherein the collection bag contains an anticoagulant and/or preservative solution.

7. A method according to claim 2, further comprising a bag containing an anticoagulant and/or preservative solution, said bag being connected via a third coupling provided in the vicinity of a collection needle on the first tube.

8. A method according to claim 2, wherein the collection bag is provided with two outlet orifices respectively provided in the top portion and in the bottom portion of the bag, first and second bags being provided to be in fluid communication with respective ones of the orifices via respective one tube.

9. A method according to claim 1, wherein first and second collection needles are provided in fluid communication with respective ones of third and fourth tubes, said third and fourth tubes being associated with the first tube via a second coupling.

10. A method according to claim 9, wherein each of the tubes is provided with a valve clamp.

11. A method according to claim 9, wherein the collection bag contains an anticoagulant and/or preservative solution.

12. A method according to claim 9, further comprising a bag containing an anticoagulant and/or preservative solution, said bag being connected via a third coupling provided in the vicinity of a collection needle on the first tube or on the fourth tube.

13. A method according to claim 9, wherein the collection bag is provided with two outlet orifices respectively provided in the top portion and in the bottom portion of the bag, first and second bags being provided to be in fluid communication with respective ones of the orifices via respective one tube.

14. A method according to claim 1, wherein each of the tubes is provided with a valve clamp.

15. A method according to claim 1, wherein the collection bag contains an anticoagulant and/or preservative solution.

16. A method according to claim 1, further including a bag containing an anticoagulant and/or preservative solution, said bag being connected via a third coupling provided in the vicinity of a collection needle on the first tube or on the fourth tube.

17. A method according to claim 1, wherein the collection bag is provided with two outlet orifices respectively provided in the top portion and in the bottom portion of the bag, first and second bags being provided to be in fluid communication with respective ones of the orifices via respective one tube.

18. A method according to claim 1, further comprising a subsequent step of removing the collection bag from the blood collection line.

19. A method according to claim 1, wherein the collection bag is then centrifuged so as to make it possible in particular to collect hematopoietic stem cells.

20. A method according to claim 1, further comprising connecting the bag containing the rinsing solution to the first tube via the second tube.

21. A method according to claim 1, further comprising inserting an anticoagulant and/or preservative solution into the collection bag.

22. A method according to claim 1, further comprising wherein the first and second tubes are interconnected via a first coupling, and
wherein first and second collection needles are provided in fluid communication with respective ones of third and fourth tubes, said third and fourth tubes being associated with the first tube via a second coupling.

23. A method according to claim 1, further comprising:
removing the collection bag from the blood collection line; and
centrifuging the collection bag to collect hematopoietic stem cells.

24. A method of collecting placental blood comprising:
connecting a bag containing a rinsing solution to a first tube via a second tube;
using a placental blood collection line comprising a collection bag in fluid communication with at least one collection needle via the first tube associated with an inlet orifice of the bag, said line further comprising the bag containing a rinsing solution;
forming a first tap into a vein of the umbilical cord or into the placenta with a needle;
collecting the placental blood in the collection bag;
emptying the bag containing the rinsing solution into the umbilical cord and into the placenta via the inserted needle of the first tap;
rinsing the placenta from which blood has been collected with the rinsing solution;
forming a second tap into the vein of the umbilical cord or into the placenta via the same needle or with another needle;
opening the first and second taps at the same time; and
collecting placental blood together with added rinsing solution in the collection bag using the second tap.

* * * * *